(12) United States Patent
Takeuchi

(10) Patent No.: US 9,968,263 B2
(45) Date of Patent: May 15, 2018

(54) PROBE, SUBJECT INFORMATION ACQUISITION APPARATUS, AND METHOD FOR MANUFACTURING THE PROBE

(71) Applicant: CANON KABUSHIKI KAISHA, Tokyo (JP)

(72) Inventor: Eiji Takeuchi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 33 days.

(21) Appl. No.: 14/477,734

(22) Filed: Sep. 4, 2014

(65) Prior Publication Data
US 2015/0073280 A1    Mar. 12, 2015

(30) Foreign Application Priority Data
Sep. 8, 2013    (JP) .................................. 2013-185795

(51) Int. Cl.
*A61B 8/00*    (2006.01)
*A61B 5/00*    (2006.01)

(52) U.S. Cl.
CPC ....... *A61B 5/0095* (2013.01); *Y10T 29/49005* (2015.01)

(58) Field of Classification Search
CPC ........................ A61B 5/0095; Y10T 29/49005
USPC ............................................. 600/437–469
See application file for complete search history.

(56) References Cited

U.S. PATENT DOCUMENTS

| 2006/0074313 | A1* | 4/2006 | Slayton | A61B 8/14 600/439 |
| 2006/0074314 | A1* | 4/2006 | Slayton | A61B 8/14 600/439 |
| 2006/0079816 | A1* | 4/2006 | Barthe | A61B 8/14 601/2 |
| 2006/0089632 | A1* | 4/2006 | Barthe | A61B 5/682 606/27 |
| 2007/0063616 | A1* | 3/2007 | Adachi | B06B 1/0622 310/311 |
| 2008/0294054 | A1* | 11/2008 | Asagiri | A61B 8/4281 600/459 |
| 2010/0160782 | A1* | 6/2010 | Slayton | A61B 5/4869 600/439 |
| 2010/0268042 | A1* | 10/2010 | Wang | A61B 5/0059 600/322 |
| 2011/0201914 | A1* | 8/2011 | Wang | A61B 5/0059 600/407 |
| 2011/0275890 | A1* | 11/2011 | Wang | A61B 5/0062 600/104 |

(Continued)

FOREIGN PATENT DOCUMENTS

JP    H08-223697 A    8/1996
JP    H11-226012 A    8/1999
(Continued)

*Primary Examiner* — Sanjay Cattungal
(74) *Attorney, Agent, or Firm* — Canon U.S.A., Inc. IP Division

(57) ABSTRACT

A probe capable of reducing positional displacement of an acoustic lens from a capacitive transducer is provided. The probe includes a transducer having elements and extraction electrodes of the elements, flexible wiring boards having wiring electrically connected to the extraction electrodes, and an acoustic lens having stepped portions which is provided on the elements. The acoustic lens is butted against end portions of the flexible wiring boards at the stepped portions and fixed.

20 Claims, 6 Drawing Sheets

(56) References Cited

U.S. PATENT DOCUMENTS

| | | | | |
|---|---|---|---|---|
| 2012/0016239 A1* | 1/2012 | Barthe | ................ | A61B 8/0858 |
| | | | | 600/439 |
| 2012/0275262 A1* | 11/2012 | Song | ................ | G01N 29/0654 |
| | | | | 367/7 |
| 2014/0276055 A1* | 9/2014 | Barthe | .................... | A61N 7/02 |
| | | | | 600/439 |
| 2015/0025420 A1* | 1/2015 | Slayton | ................ | A61B 8/483 |
| | | | | 601/2 |

FOREIGN PATENT DOCUMENTS

| | | |
|---|---|---|
| JP | 2008-119318 A | 5/2008 |
| WO | 2008/114582 A1 | 9/2008 |
| WO | 2009/139400 A1 | 11/2009 |

\* cited by examiner

XX' CUT SECTION

PROBE, SUBJECT INFORMATION ACQUISITION APPARATUS, AND METHOD FOR MANUFACTURING THE PROBE

BACKGROUND OF THE INVENTION

Field of the Invention

The present invention relates to a probe, a subject information acquisition apparatus having the prove, and a method for manufacturing the probe.

Description of the Related Art

As ultrasonic diagnostic devices, devices using photoacoustic waves are provided. The photoacoustic waves are, for example, ultrasound waves produced when a pulse laser (electromagnetic wave) emitted from the outside of a body is absorbed in tissue in the body. Since the photoacoustic waves are produced in specific tissue in the body, imaging of the body tissue using the information of the photoacoustic waves can be performed. Sound waves, ultrasonic waves, photoacoustic waves, and other waves are referred to as acoustic waves. In this specification, they may be represented by the ultrasonic waves.

For detection of the ultrasonic waves produced in the body, a probe can be used. In the probe, an ultrasonic transducer is provided to convert the ultrasonic waves into electrical signals. Conventionally, the ultrasonic transducers using the piezoelectric effect have been used. In recent years, capacitive transducers have also been actively studied and developed. The capacitive transducer includes, for example, cells each having two electrodes provided to sandwich a gap referred to as a cavity maintained in a near-vacuum state, and includes at least one element having at least one cell. One of the two electrodes is fixed to a membrane, and the vibrating membrane having such a structure is held in a state the membrane can vibrate. Vibration of the vibrating membrane by ultrasonic waves changes the distance between the two electrodes, and this causes a change in the capacitance. When voltage is applied between the two electrodes, the capacitance is changed, which is taken out as an electric signals. This is a principle of the ultrasonic wave reception operation. Further, the application of the voltage between the two electrodes also produces the electrostatic attraction. By temporally varying the application voltage, the vibrating membrane vibrates. This is a principle of the ultrasonic wave transmission operation. Among the capacitive transducers, transducers manufactured by applied semiconductor microfabrication techniques are referred to as capacitive micromachined ultrasonic transducers (CMUTs). Probes having a plurality of capacitive transducers (that is, the cells and elements) arrayed at high densities are suitable to achieve high image quality needed in the ultrasonic diagnostic devices.

In the above-described technical field, probes having an acoustic lens disposed on an ultrasonic transducer are proposed (for example, see Japanese Patent Application Laid-Open No. 2008-119318). Further, in the probes having an acoustic lens, a probe in which an anisotropic adhesive and an ultrasonic transducer are electrically connected is provided (see WO2008/114582). In the probes, it is preferable that the acoustic lens is fixed to a capacitive transducer (that is, cells or elements) without positional displacement. The acoustic lens, however, often uses a soft member, for example, silicone rubber, and even though the acoustic lens is positioned at a part of the acoustic lens, the acoustic lens may positionally deviate at the other parts.

SUMMARY OF THE INVENTION

The present invention is directed to providing a probe in which positional displacement of an acoustic lens from a capacitive transducer is reduced.

According to an aspect of the present invention, a probe includes a transducer having elements and extraction electrodes of the elements, flexible wiring boards having wiring electrically connected to the extraction electrodes, and an acoustic lens having stepped portions which is provided on the elements. The acoustic lens is butted against end portions of the flexible wiring boards at the stepped portions and fixed.

Further features of the present invention will become apparent from the following description of exemplary embodiments with reference to the attached drawings.

DESCRIPTION OF THE EMBODIMENTS

Various exemplary embodiments, features, and aspects of the invention will be described in detail below with reference to the drawings.

A probe according to an exemplary embodiment of the present invention include an acoustic lens provided on elements of a transducer of, for example, a capacitive type. The acoustic lens includes a stepped portion having an L-shaped portion defined by two surfaces. At the stepped portion, the acoustic lens butts against end portions of flexible wiring boards. While the exemplary embodiment of the present invention will be described based on the above-described thought, it is to be understood that the invention is not limited to the exemplary embodiment, various modifications and changes can be made within the scope of the invention.

Figure 1:
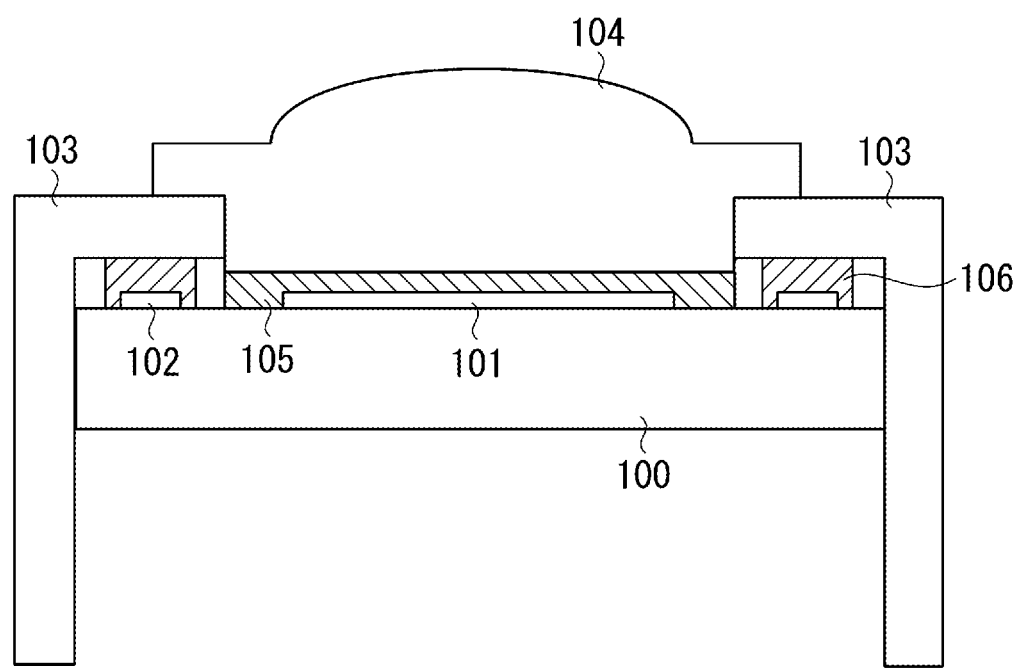
FIG. 1 is a cross sectional view illustrating an exemplary embodiment of the present invention.
Figure 2:
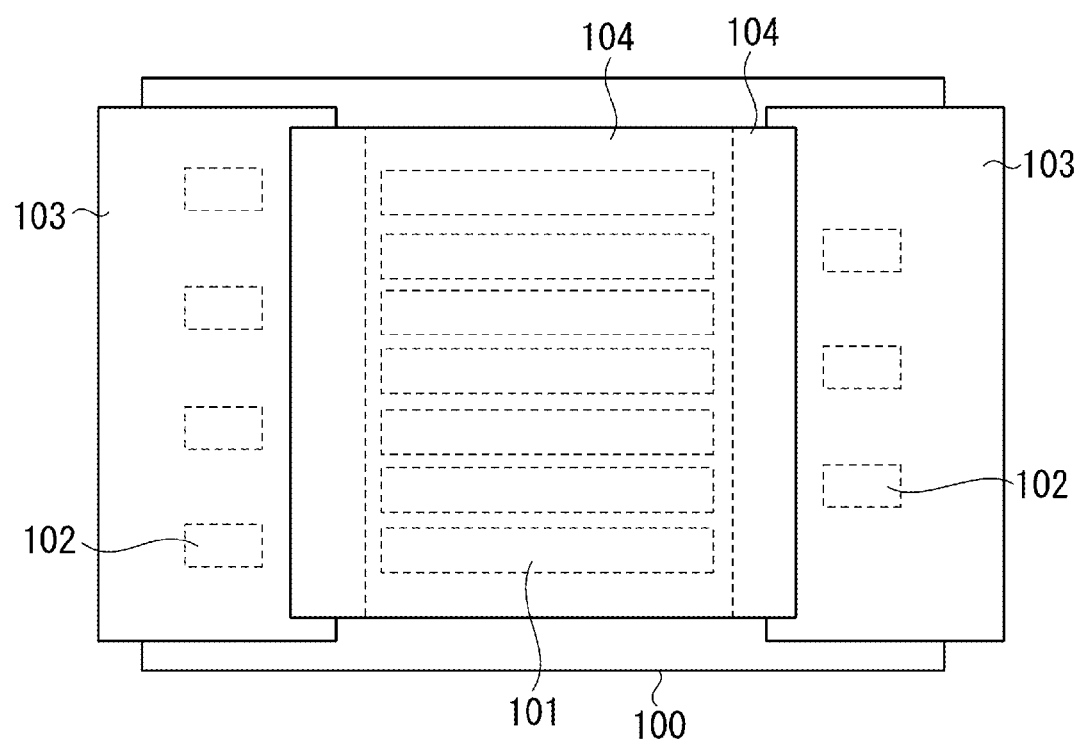
FIG. 2 is a top view illustrating the exemplary embodiment of the present invention.

Hereinafter, the exemplary embodiment of the present invention will be described with reference to the attached drawings. FIG. 1 is a cross sectional view illustrating the first exemplary embodiment of the present invention. On a substrate 100, elements 101 having a plurality of cells are one-dimensionally or two-dimensionally arrayed. In this exemplary embodiment, as illustrated in FIG. 2, which is a top view, the elements 101 are one-dimensionally (in the vertical direction in FIG. 2) arrayed. Extraction electrodes 102 of the element 101 are disposed at edge portions on the substrate 100. At peripheral portions of the substrate 100, flexible wiring boards 103 having wiring electrically connected to the extraction electrodes 102 are disposed. In this exemplary embodiment, the flexible wiring boards 103 are disposed at both the right and left sides of the substrate 100 in a bent state. To connect the extraction electrodes 102 and the flexible wiring boards 103, for example, an anisotropic conductive film (ACF) 106 is used, however, as long as the electrodes and the boards can be connected at a low resistance, any connection method can be employed. When the anisotropic conductive film is used, the step of the stepped portion can be lowered.

On the element 101, an acoustic lens 104 having the stepped portion is disposed. In this exemplary embodiment, the stepped portion has an L-shaped portion defined by two surfaces extending at right angles to one another. The acoustic lens 104 butts against end portions of the flexible wiring boards 103, and the acoustic lens is fixed to the substrate 100 using an adhesive 105. More specifically, the side surface of the end portion of the wiring board 103 butts against one surface (the surface extending in the vertical direction in FIG. 1) of the L-shaped portion of the stepped portion, and the upper surface of the end portion of the wiring board 103 is in contact with another surface (the surface extending in the horizontal direction in FIG. 1) of the L-shaped portion of the stepped portion. Such a butt structure is configured on at least one of the right and left sides of the acoustic lens 104 in the drawing, and thereby the acoustic lens is fixed.

FIG. 2 is a top view of the above-described structure. In the drawing, an example of the extraction electrodes 102 alternately disposed at right and left sides is illustrated. Alternatively, the extraction electrodes 102 can be disposed on only one side of the right and left sides. In such a case, the butt structure is provided on only one side of the right and left sides. Consequently, the position of the stepped portion at the other side of the acoustic lens 104 is defined, for example, by an end portion of a case. Alternatively, the stepped portion may be omitted at the other side of the acoustic lens 104, and a simple side surface can be provided. The position of the side surface can be defined by an end portion of a case.

Hereinafter, reasons for the reduction in positional displacement of the acoustic lens from the capacitive transducer will be described. The positioning accuracy in connecting the flexible wiring boards 103 to the extraction electrodes 102 can be sufficiently reduced, and if alignment marks are used, for example, the flexible wiring boards 103 can be fixed to the extraction electrodes 102 at an accuracy of 100 micrometers or less. Further, both the extraction electrodes 102 and the elements 101 are patterns in the substrate fabricated by semiconductor processes, and the positional displacements of the electrodes and elements are small. Consequently, to the elements 101, the flexible wiring boards 103 can be fixed at a high accuracy, and similarly, the acoustic lens 104 butting against the flexible wiring boards 103 can be fixed to the elements 101 at a high accuracy.

In this exemplary embodiment, the butting of the acoustic lens 104 is performed near the capacitive transducer to increase the positioning accuracy. As compared to the technique for fitting an acoustic lens outside (at the side surface) of the substrate, for example, the technique discussed in Japanese Patent Application Laid-Open No. 2008-119318 defines a position of the acoustic lens at a position near the transducer, which can reduce an amount of positional displacement due to deformation of the lens. This method can increase the positioning accuracy. Meanwhile, to reduce the size of the probe, materials are to be used to the minimum to fix the acoustic lens. As described in this exemplary embodiment, the small probe can be provided by using the flexible wiring boards necessary for transmission or reception to position the acoustic lens.

As described above, the number of the stepped portions of the acoustic lens butting against the flexible wiring boards can be one or more. The butting direction can be one of the horizontal direction, the back and forth direction, and the vertical direction. Both one and more butting directions enable the increase of the positioning accuracy, and the number of the directions is not limited to any one of the directions. Further, it is not always necessary that the entire surface of the stepped portion of the acoustic lens butts against the flexible wiring board, and the stepped portion may butt at least two portions. The above-described probe according to the exemplary embodiment butts and is fixed to the end portions of the flexible wiring boards at the stepped portions of the acoustic lens, and this enables the reduction in the positional displacement of the acoustic lens from the transducer.

The above-described structure can be described as follows. That is, the probe has a substrate of a rectangle and a protrusion of an acoustic lens is provided to fit into a recessed portion formed by the substrate and end portions of flexible wiring boards disposed in at least a pair of two sides facing to each other of the substrate. The bottom surface of the protrusion is bonded to the substrate. In such a structure, the positioning and bonding of the acoustic lens can be readily and surely performed.

Figure 3A:
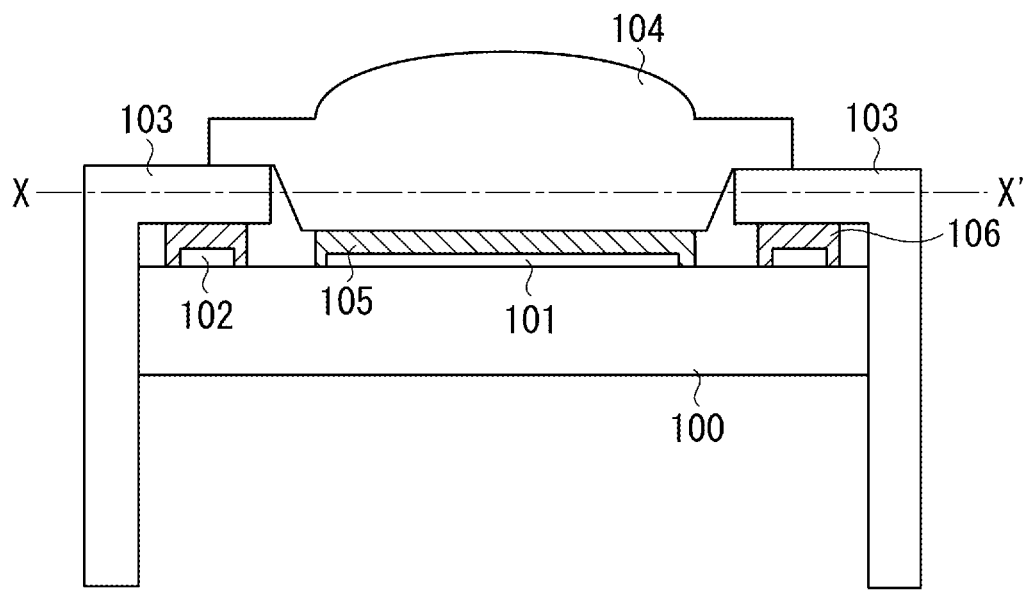
FIGS. 3A and 3B are cross sectional views illustrating another exemplary embodiment of the present invention.
Figure 3B:
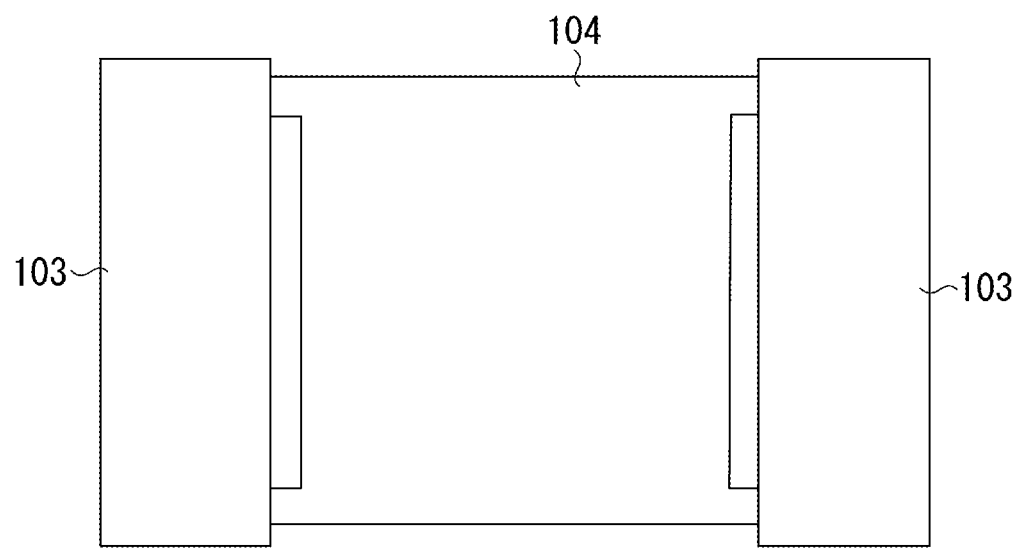

The structure can also be formed as described below. That is, recessed portions (see FIG. 3) for receiving a protrusion of the anisotropic conductive film that may be formed when bonding the substrate and the flexible wiring boards are provided to the acoustic lens so that the protrusion does not prevent the butting of the flexible wiring boards and the acoustic lens. For example, the stepped portion of the acoustic lens can be formed in an L-shaped portion of an obtuse angle illustrated in FIG. 3. This prevents the protrusion of the anisotropic conductive film from entering the recessed portions formed by the stepped portions and the end portions of the flexible wiring boards, and hindering the butting of the flexible wiring boards and the acoustic lens. Consequently, decrease in the accuracy in positioning the acoustic lens can be reduced. It is preferable that such recessed portions are provided in the end portions of the acoustic lens. However, alternatively, grooves that serve as the recessed portions for receiving the protrusion of the anisotropic conductive film may be provided in the substrate 100. The positions and shapes of the recessed portions are not limited to the above-described positions and shapes. As described above, in this exemplary embodiment, the acoustic lens is placed such that the protrusion of the anisotropic conductive film formed when bonding the substrate and the flexible wiring boards is received by the recessed portions formed by the stepped portions and the end portions of the flexible wiring boards, or the recessed portions formed in the substrate.

The above-described apparatus can be manufactured, for example, according to a manufacturing method including the following steps. First, the extraction electrodes of the elements are electrically connected to corresponding wiring of the flexible wiring boards via the anisotropic conductive film, or the like. Then, the acoustic lens is positioned by fitting the protrusion (i.e., the portion defined by the stepped portions) into the recessed portion formed by the end portions of the flexible wiring boards and the substrate to make the acoustic lens contact the adhesive. The acoustic lens and the substrate are pressed and heated while being pressed to bond the acoustic lens onto the transducer.

Figure 4A:
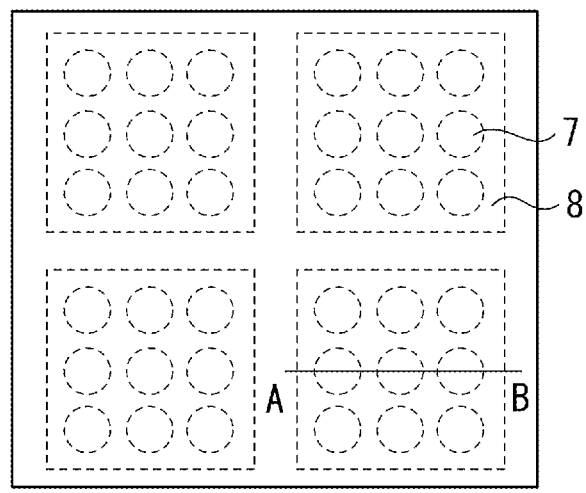
FIGS. 4A and 4B illustrate an example of a capacitive transducer.
Figure 4B:
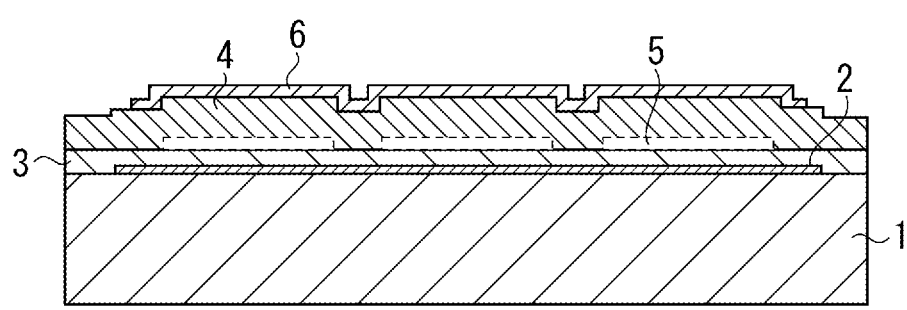

Hereinafter, a capacitive transducer that is an example of the transducer used in this exemplary embodiment is described. FIGS. 4A and 4B illustrate an example of the capacitive transducer including elements having a plurality of cells. FIG. 4A is a top view, and FIG. 4B is a cross-sectional view taken along the line A-B in FIG. 4A. This transducer includes a plurality of elements 8 (corresponding to the elements 101 in FIG. 2) having cell structures 7. In FIGS. 4A and 4B, each of the four elements 8 includes nine cells 7. However, the number of the cells is not limited as long as each of the elements 8 includes at least one cell. An array form of the cells in the element 101 in FIG. 2 does not necessarily need to be the same as the array form of the cells 7 in the element 8 in FIGS. 4A and 4B.

The cell 7 according to the exemplary embodiment includes, as illustrated in FIG. 4B, a substrate 1 (corresponding to the substrate 100 in FIG. 1), a first electrode 2, an insulating film 3 on the first electrode 2, a vibrating membrane 4 supported via the insulating film 3 and a gap (an air gap, or the like) 5 such that the membrane can vibrate, and a second electrode 6 on the vibrating membrane 4. The substrate 1 is formed of Si. Alternatively, the substrate 1 can be formed of an insulating substrate such as glass. The first electrode 2 is formed of a metal film of, for example, titanium or aluminum. When the substrate 1 is formed of low-resistance silicon, the substrate 1 itself can serve as the first electrode 2. The insulating film 3 can be formed by depositing a thin film of, for example, silicon oxide. The vibrating membrane 4 and a portion for supporting the vibrating membrane 4 are formed by depositing a thin film of, for example, silicon nitride. The second electrode 6 can be formed of a metal film of, for example, titanium or aluminum. The vibrating film made of the membrane portion formed of the silicon nitride and the single crystal silicon film and the second electrode portion can be combined and considered as a vibrating membrane. As described above, in this exemplary embodiment, the element includes at least one cell having the structure in which the vibrating membrane including one of the two electrodes provided across a gap is supported in a manner that the vibrating membrane can vibrate.

The principles of the drive of the transducer according to the exemplary embodiment will be described. The cell includes the first electrode 2 and the vibrating membrane provided across gaps 5 between the first electrode and the vibrating membrane. Consequently, to receive acoustic waves, direct voltage is to be applied to the first electrode 2 or the second electrode 6. The bias voltage is applied from a voltage application portion. When acoustic waves are received, the acoustic waves cause the vibrating membrane to vibrate to change the length (height) of the gap. This changes the capacitance between the electrodes. The capacitance change is detected from the first electrode 2 or the second electrode 6 and thereby the acoustic waves can be detected. The reception signal by the capacitance change is sent to an amplifier circuit. The element can send acoustic waves by applying alternating voltage to the first electrode 2 or the second electrode 6 to vibrate the vibrating membrane. Such a transmission signal of the alternating voltage is sent from a transmission/reception circuit to the element 8.

In this exemplary embodiment, the surface of the acoustic lens 104 has an arch shape extending in the vertical direction in FIG. 1. Consequently, with respect to the horizontal direction in FIG. 1, by the power of the curvature of the acoustic lens 104, the beams of the acoustic waves are converged. With respect to the vertical direction in FIG. 1, the acoustic lens 104 does not have power, and a beamforming transmission and reception method is employed. In this method, a limited predetermined number of sets of the elements among the total number of the transmittable and receivable channels are changed by sequentially applying delays in the vertical direction of the drawing to form one beam and perform scan to obtain information of ultrasonic waves of a subject in the beam direction in each time point. After the formation of one beam and acquisition of the ultrasonic wave information of the subject in the beam direction in the sets of the elements in the one-dimensional or two-dimensional arrays, further, the ultrasonic wave information of the subject in the beam direction is obtained by shifting by one element in the row or line direction. This operation is sequentially performed to combine the information to form an image, for example, an image called B (brightness) mode image. In the ultrasonic wave transmission and reception system that performs this operation, signal transmission and reception is performed between the elements of the channel and the circuit used in the beamforming, however, the signal transmission and reception is not performed between the elements and the circuit that are not used. It is to be understood that depending on a required function, the surface of the acoustic lens 104 can have the other shapes such as a spherical shape.

Hereinafter, a more specific first exemplary embodiment is described. In this exemplary embodiment, on a silicon wafer, a plurality of capacitive transducers and extraction electrodes are formed by semiconductor processes. From the silicon wafer, substrates of 50 mm long and 10 mm wide are cut. The elements 101 are one-dimensionally arrayed in the vertical direction. The extraction electrodes 102 are disposed at left or right of corresponding capacitive transducers respectively.

This structure is described with reference to FIG. 1. The flexible wiring boards 103 with copper wiring of a thickness of 10 μm are insulated by polyimide of 50 μm at both sides of upper and bottom portions except for portions contacting the extraction electrodes 102. On the extraction electrodes 102 disposed around the substrate 100, the anisotropic conductive film 106 is coated, and on the film, the flexible wiring boards 103 are aligned. Then, the flexible wiring boards are pressed from the top to fix the boards. Then, thermal curing is performed onto the anisotropic conductive film at 80° C. to bond the extraction electrodes 102 and the wiring on the flexible wiring boards 103. The flexible wiring boards are bonded to both left and right sides of the substrate 100. After bonding, each positional displacement of the extraction electrodes 102 and the wiring of the flexible wiring boards 103 was measured. A positional displacement in the vertical direction (the extending direction of the wiring) was 50 μm at the maximum, and a positional displacement in the horizontal direction (the direction perpendicular to the extending direction of the wiring in the plane) was 20 μm at the maximum.

The acoustic lens 104 is formed of silicone, and has a convex step of 100 μm at the lower part, and has a lens shape of the radius of curvature of 14 mm at the upper part. On the capacitive transducer, the adhesive 105 of a thickness of 20 μm is applied, and the convex stepped portion of the acoustic lens 104 is inserted into a gap between the right and left flexible wiring boards 103 to butt one sides of the flexible wiring boards 103 and the acoustic lens 104 to fix the lens. While the acoustic lens 104 is pressed from the top, thermal curing is performed to the adhesive at 80° C. to bond the acoustic lens 104 to the substrate 100.

In the probe manufactured in the above-described method, cross sections were taken at five points, and displacements of the central axis (the axis extending in the vertical direction in FIG. 1) of the acoustic lens 104 and the central axis (the axis extending in the vertical direction in FIG. 1) of the capacitive transducer were measured. As a result, a maximum positional displacement of the acoustic lens and the capacitive transducer was 20 μm. In the above-described exemplary embodiment, the elements 101 of the capacitive transducer are one-dimensionally arrayed. Alternatively, when the capacitive transducers are two-dimensionally arrayed, the positioning fixation can be similarly performed.

<Other Exemplary Embodiments>

The above-described capacitive transducer can be applied to subject information acquisition apparatuses such as ultrasonic diagnostic devices. Acoustic waves from a subject are received by the transducer, and using output electrical signals, subject information reflecting optical characteristic values of the subject such as a light absorption coefficient and information reflecting differences in acoustic impedance can be acquired.

More specifically, an example of the information acquisition apparatuses irradiates a subject with light (visible light or electromagnetic waves including infrared light). This enables reception of photoacoustic waves generated at a plurality of positions (portions) in the subject, and a character distribution indicating a distribution of the characteristic information corresponding to the individual positions in the subject is acquired. The characteristic information acquired by the photoacoustic waves indicates information relating to the absorption of the light. The characteristic information includes information reflecting an initial sound pressure of the photoacoustic waves generated by the light irradiation, a light energy absorption density derived from the initial sound pressure, an absorption coefficient, a density of the substances forming the tissue, and the like. The density of the substances is, for example, a degree of oxygen saturation, a total hemoglobin concentration, an oxyhemoglobin concentration, or a deoxyhemoglobin concentration. In addition, the information acquisition apparatuses can be used for diagnosis of malignant tumors or vascular diseases of humans and animals, or chemical treatment follow-up. Accordingly, as a target subject, a living body is conceivable, more specifically, a target part for diagnosis such as a breast, a cervix, or an abdomen of a human or an animal can be considered. The light absorbers in the subject body include tissues having relatively high absorption coefficients in the subject body. For example, when a subject is a part of the human body, the light absorbers can be oxyhemoglobin or deoxyhemoglobin, blood vessels containing much oxyhemoglobin or deoxyhemoglobin, tumors containing many newborn blood vessels, or plaque on a carotid wall. Further, the light absorbers can be molecular probes specifically combined with malignant tumors, or the like, by means of gold particles, graphite, or the like, or capsules that transmit medicine.

Further to the reception of photoacoustic waves, a distribution relating to acoustic characteristics in a subject can be acquired by receiving reflected waves generated as ultrasonic echo which are sent from probes containing transducers in the subject. The distribution relating to the acoustic characteristics contains a distribution reflecting an acoustic impedance difference in the tissues in the subject.

Figure 5A:
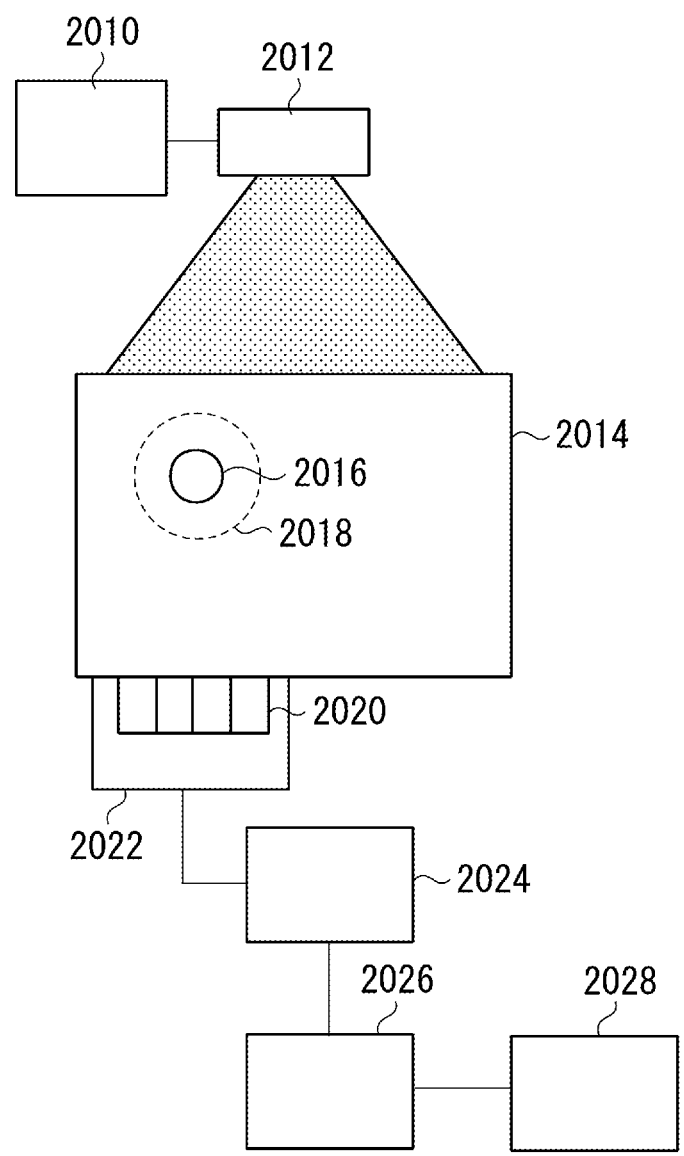
FIGS. 5A and 5B are block diagrams illustrating overall structures of information acquisition apparatuses having a probe according to the exemplary embodiments of the present invention.

FIG. 5A illustrates an information acquisition apparatus using the photoacoustic effects. A subject 2014 is irradiated with pulse light emitted by a light source 2010, via optical members 2012 such as lenses, mirrors, and optical fibers. A light absorber 2016 in the subject 2014 absorbs the energy of the pulse light, and generates photoacoustic waves 2018 that are acoustic waves. A transducer 2020 according to the exemplary embodiment of the present invention in a probe portion 2022 receives the photoacoustic waves 2018 and converts the waves into electrical signals, and outputs the signals to a front-end circuit in the probe portion. The front-end circuit performs signal processing such as preamplyfying processing, and sends the signals to a signal processing unit 2024 in a body unit via a connection unit. The signal processing unit 2024 performs signal processing such as analog-to-digital conversion (A/D conversion) and amplification on the input electrical signals, and outputs the signals to a data processing unit 2026 in the body unit. The data processing unit 2026 acquires the subject information (characteristic information reflecting the optical characteristic values of the subject such as a light absorption coefficient) using the input signals as image data. In this description, the signal processing unit 2024 and the data processing unit 2026 are together referred to as a processing unit. A display unit 2028 displays an image based on the image data input from the data processing unit 2026. The probe portion 2022 and the body unit can be integrally formed.

Figure 5B:
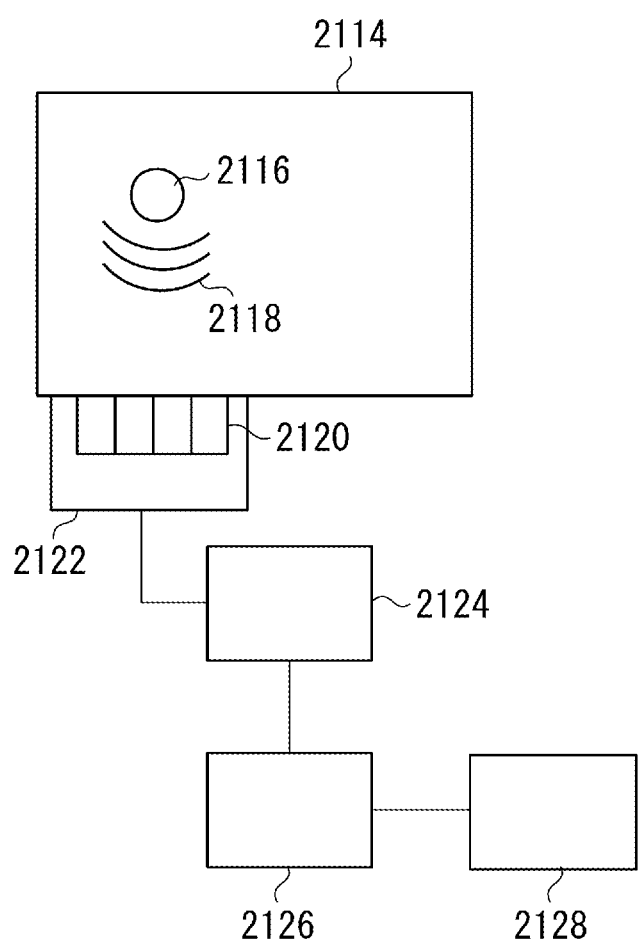

FIG. 5B illustrates an information acquisition apparatus such as an ultrasonic echo diagnostic device using reflection of acoustic waves. Acoustic waves sent to a subject 2114 from a transducer 2120 within a probe portion 2122 according to the exemplary embodiment of the present invention are reflected by a reflector 2116. The transducer 2120 receives the reflected acoustic waves (reflected waves) 2118 and converts the waves into electrical signals, and outputs the signals to a front-end circuit in the probe portion. The front-end circuit performs signal processing such as preamplyfying processing, and sends the signals to a signal processing unit 2124 in a body unit via a connection unit. The signal processing unit 2124 performs on the input electrical signals signal processing such as A/D conversion and amplification, and outputs the signals to a data processing unit 2126 in the body unit. The data processing unit 2126 acquires the subject information (characteristic information reflecting the difference in the acoustic impedance) using the input signals as image data. In this description, the signal processing unit 2124 and the data processing unit 2126 are also referred to as a processing unit. A display unit 2128 displays an image based on the image data input from the data processing unit 2126. The probe portion 2122 and the body unit can be integrally formed.

The probe unit can be a unit which mechanically performs scanning, or a unit (handheld type) that is moved to the subject by a user such as a doctor and operator. In the apparatus using the reflected waves as illustrated in FIG. 5B, the probe for sending acoustic waves can be provided separately from the probe for receiving acoustic waves. Further, an apparatus having the functions of both the apparatuses illustrated in FIGS. 5A and 5B can be provided, and both of the subject information reflecting optical characteristic values of a subject and the subject information reflecting differences in acoustic impedance can be acquired. In such a case, the transducer 2020 in FIG. 5A may receive not only the photoacoustic waves, but also transmit acoustic waves and receive reflected waves.

In the probe according to the exemplary embodiments of the present invention, the acoustic lens is butted and fixed to the end portions of the flexible wiring boards at the stepped portion, which enables the reduction in the positional displacement of the acoustic lens and the capacitive transducer.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-185795 filed Sep. 8, 2013, which is hereby incorporated by reference herein in its entirety.

What is claimed is:

1. A probe comprising:
    a transducer having elements and extraction electrodes of the elements;
    flexible wiring boards having wiring electrically connected to the extraction electrodes;
    an acoustic lens having stepped portions, the acoustic lens being provided on the elements; and
    a substrate to support the elements and the extraction electrodes,
    wherein the acoustic lens is butted against end portions of the flexible wiring boards in a contact state at the stepped portions and fixed,
    wherein the flexible wiring boards are disposed at edge portions on the substrate in a bent state, and
    wherein a protrusion defined by the stepped portions of the acoustic lens is provided to fit into a recessed portion formed by the substrate and end portions of the flexible wiring boards disposed in at least a pair of two edge sides of the substrate, and the bottom surface of the protrusion is bonded to the substrate.

2. The probe according to claim 1, wherein the wiring of the flexible wiring boards is bonded to the extraction electrodes by an anisotropic conductive film.

3. The probe according to claim 2, wherein the acoustic lens is mounted such that a protrusion of the anisotropic conductive film formed when bonding the substrate and the flexible wiring boards is received by recessed portions formed by the stepped portions and the end portions of the flexible wiring boards, or recessed portions formed in the substrate.

4. The probe according to claim 1, wherein the element includes at least one cell having a vibrating membrane including a first electrode, and a second electrode provided across a gap between the first electrode and the second electrode.

5. A method for manufacturing the probe according to claim 1, the method comprising:
    electrically connecting the extraction electrodes to the wiring of the flexible wiring boards via an anisotropic conductive film;
    applying an adhesive on the transducer;
    positioning the acoustic lens by fitting a protrusion of the acoustic lens into a recessed portion formed by the end portions of the flexible wiring boards and a substrate, so as to make the acoustic lens contact the adhesive; and
    bonding the acoustic lens onto the transducer by heating the acoustic lens and the substrate while applying pressure to press the acoustic lens and the substrate.

6. A subject information acquisition apparatus comprising:
    the probe according to claim 1; and
    a processing unit configured to acquire information of a subject using electric signals output from the probe,
    wherein the probe receives acoustic waves from the subject, and outputs the electrical signals.

7. A subject information acquisition apparatus comprising:
    the probe according to claim 1;
    a light source; and
    a processing unit,
    wherein the probe receives acoustic waves generated by irradiating a subject with the light emitted from the light source and converts the acoustic waves into electric signals, and
    wherein the processing unit acquires information of the subject using the electric signals.

8. The probe according to claim 1, wherein each of the elements has a plurality of cells.

9. The probe according to claim 1, wherein the elements are one-dimensionally or two-dimensionally arrayed.

10. A probe comprising:
    a transducer having elements and extraction electrodes of the elements;
    a flexible wiring board having wiring electrically connected to the extraction electrodes;
    an acoustic lens having a stepped portion, the acoustic lens being provided over the elements; and
    a substrate to support the elements and the extraction electrodes, wherein the acoustic lens is positioned based on an end portion of the flexible wiring board at the stepped portion and fixed.

11. The probe according to claim 10, wherein the acoustic lens is butted against end portions of the flexible wiring board.

12. The probe according to claim 11, wherein the stepped portion of the acoustic lens is butted against end portions of the flexible wiring board.

13. The probe according to claim 10, wherein the flexible wiring board is disposed above the substrate and extended to a side of the substrate in a bent state.

14. The probe according to claim 10, wherein the acoustic lens is fixed to the substrate using an adhesive.

15. The probe according to claim 10, wherein the flexible wiring board is connected to the extraction electrodes using an anisotropic conductive film.

16. The probe according to claim 10, wherein each of the elements has a rectangular shape.

17. The probe according to claim 16, wherein the elements are one-dimensionally arrayed.

18. The probe according to claim 16, wherein the surface of the acoustic lens has an arch shape extending in the one-dimensionally arrayed direction.

19. The probe according to claim 10, wherein the transducer is a capacitive type transducer.

20. A subject information acquisition apparatus comprising:
    the probe according to claim 10; and
    a processing unit configured to acquire information of a subject using electric signals output from the probe,
    wherein the probe receives acoustic waves from the subject, and outputs the electrical signals.

* * * * *